US011648201B2

(12) United States Patent
Sonavane et al.

(10) Patent No.: US 11,648,201 B2
(45) Date of Patent: May 16, 2023

(54) PHARMACEUTICAL FORMULATIONS

(71) Applicant: Ferring B.V., Hoofddorp (NL)

(72) Inventors: Ganeshchandra Sonavane, Maharashtra (IN); Parag Lokhande, Maharashtra (IN); Pradeep Sethi, Odisha (IN); Tushar Wagh, Maharashtra (IN)

(73) Assignee: Ferring B.V., Hoofddorp (NL)

( * ) Notice: Subject to any disclaimer, the term of this patent is extended or adjusted under 35 U.S.C. 154(b) by 0 days.

(21) Appl. No.: 17/051,732

(22) PCT Filed: Apr. 25, 2019

(86) PCT No.: PCT/EP2019/060605
§ 371 (c)(1),
(2) Date: Oct. 29, 2020

(87) PCT Pub. No.: WO2019/211159
PCT Pub. Date: Nov. 7, 2019

(65) Prior Publication Data
US 2021/0236426 A1    Aug. 5, 2021

(30) Foreign Application Priority Data

May 2, 2018    (IN) .............................. 201811016594

(51) Int. Cl.
*A61K 9/16*    (2006.01)
*A61K 31/4545*    (2006.01)
(Continued)

(52) U.S. Cl.
CPC .......... *A61K 9/1623* (2013.01); *A61K 9/1664* (2013.01); *A61K 9/1682* (2013.01);
(Continued)

(58) Field of Classification Search
CPC ............ A61K 31/4545; A61K 31/4725; A61K 9/1635; A61K 9/1664; A61K 31/519;
(Continued)

(56) References Cited

U.S. PATENT DOCUMENTS 7,122,198 B1 * 10/2006 Singh ................... A61K 9/0056
424/401
2009/0004270 A1    1/2009 Wehling et al.
(Continued)

FOREIGN PATENT DOCUMENTS

EP    0 999 843 B1    5/2000
RU    2175554 C2    11/2001
(Continued)

OTHER PUBLICATIONS

Office Action dated Jan. 12, 2022, in Russian Application No. 2020139144.
(Continued)

*Primary Examiner* — Jianfeng Song
(74) *Attorney, Agent, or Firm* — Foley & Lardner LLP

(57) ABSTRACT

A free-flowing solid pharmaceutical formulation comprising one or more active ingredients and a blend comprising sorbitol and liquid paraffin, a package containing the formulation, a process for the manufacture of the formulation and the use of the blend in the formulation.

24 Claims, 8 Drawing Sheets

Figure 1:
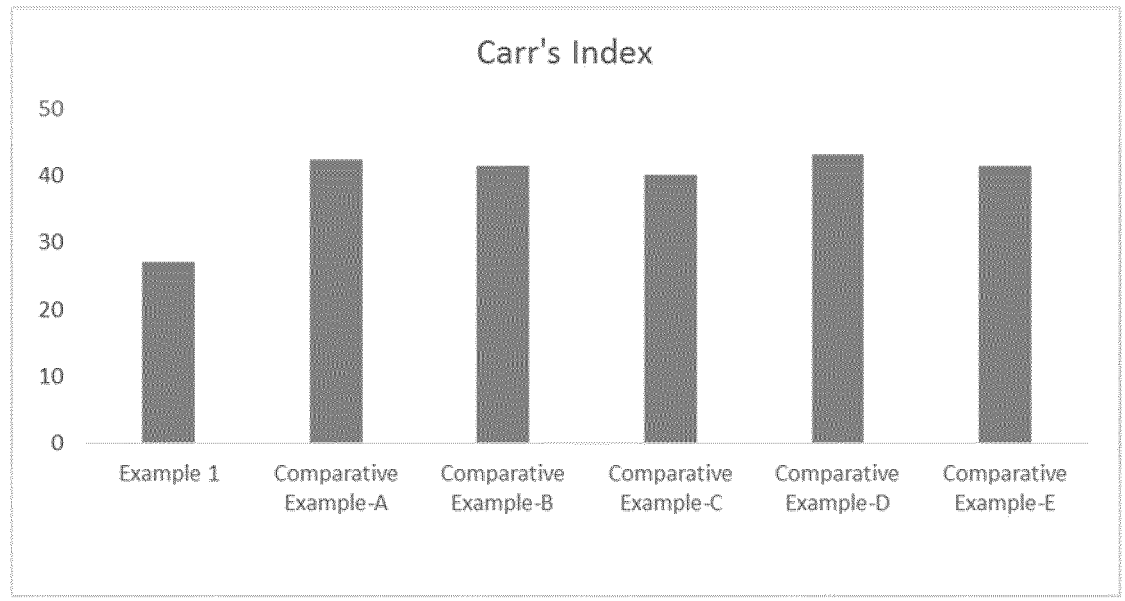

(51) Int. Cl.
*A61K 31/519* (2006.01)
*A61K 31/4725* (2006.01)
*A61K 9/19* (2006.01)

(52) U.S. Cl.
CPC ............ *A61K 9/19* (2013.01); *A61K 31/4545* (2013.01); *A61K 31/4725* (2013.01); *A61K 31/519* (2013.01)

(58) Field of Classification Search
CPC ...... A61K 9/5084; A61K 9/19; A61K 9/0056; A61K 9/0095; A61K 9/1682; A61K 9/1623
See application file for complete search history.

(56) References Cited

U.S. PATENT DOCUMENTS

| | | | | |
|---|---|---|---|---|
| 2009/0247575 | A1* | 10/2009 | Asotra | A61K 9/5026 514/311 |
| 2010/0129310 | A1 | 5/2010 | Mehta et al. | |
| 2010/0310668 | A1* | 12/2010 | Paetz | A61K 31/404 424/490 |
| 2015/0080353 | A1* | 3/2015 | Singh | A61K 9/5146 514/165 |
| 2016/0128944 | A1 | 5/2016 | Chawrai et al. | |

FOREIGN PATENT DOCUMENTS

| | | | |
|---|---|---|---|
| RU | 2454221 C2 | 6/2012 | |
| WO | WO-2006/092207 | 9/2006 | |
| WO | WO-2008/110599 | 9/2008 | |
| WO | WO-2009/112156 A1 | 9/2009 | |
| WO | WO-2009112156 A1 * | 9/2009 | ............ A61K 45/06 |
| WO | WO-2010/021607 A2 | 2/2010 | |
| WO | WO-2012/099260 | 7/2012 | |
| WO | WO-2013/077829 A1 | 5/2013 | |

OTHER PUBLICATIONS

Search Report dated Jan. 12, 2022, in Russian Application No. 2020139144.
Office Action dated Jan. 10, 2023 in Taiwan Patent Application No. 108115070.

* cited by examiner

PHARMACEUTICAL FORMULATIONS

CROSS-REFERENCE TO RELATED APPLICATIONS

The present application is the U.S. National Stage of International Application PCT/EP2019/060605, filed Apr. 25, 2019, and claims priority to Indian Patent Application No. 201811016594, filed May 2, 2018.

FIELD OF THE INVENTION

The present invention relates to pharmaceutical formulations, to methods of making them and to their use in the treatment and prophylaxis of diseases in mammals, particularly humans.

BACKGROUND OF THE INVENTION

Pharmaceutical dosage forms which rapidly dissolve when placed in the mouth of the patient, thereby delivering the desired dose of the pharmaceutically active substances, are particularly useful when the dosage form can be taken without water. Such dosage forms are generally preferred by children and old people and also by people with difficulties in swallowing and/or taking tablets or capsules.

Rapidly dissolving dosage forms are generally prepared using a multistep process. Some of these processes use a lyophilization step during which solvent is removed from a solution and/or suspension comprising a pharmaceutically active substance, carrier material and solvent.

Pharmaceutical formulations manufactured by lyophilization have various advantages but also various challenges such as issues of free flow, moisture absorption, bitter taste, dose uniformity and content uniformity. The present invention aims at overcoming these challenges.

SUMMARY OF THE INVENTION

The present invention provides a novel blend composition of sorbitol and liquid paraffin for use in the improvement of formulation properties of pharmaceutical formulations in several parameters, i.e. flow properties, moisture protection, antistatic properties and compressibility (Carr Index). The blend composition may also contain citric acid and has the ability to mitigate the taste of bitter drugs.

The present invention thus provides a free-flowing solid pharmaceutical formulation comprising one or more active ingredients and a blend composition comprising or consisting of sorbitol, liquid paraffin and optionally citric acid.

The present invention further provides a blend, comprising or consisting of sorbitol, liquid paraffin and optionally citric acid, for use in the manufacture of a pharmaceutical formulation comprising one or more active ingredients.

The present invention also provides a process for the manufacture of a solid pharmaceutical formulation of the invention comprising:
(a) forming a lyophilized powder by subliming the solvent from a preparation comprising one or more active ingredients and the solvent;
(b) forming a blend composition comprising or consisting of sorbitol, liquid paraffin and optionally citric acid;
(c) mixing the blend composition obtained in step (b) with the lyophilized powder obtained in step (a).

FIGURES

FIG. 1 compares the Compressibility Index (Carr Index) of the formulations of Example 1 and Comparative Examples A-E.

Figure 2:
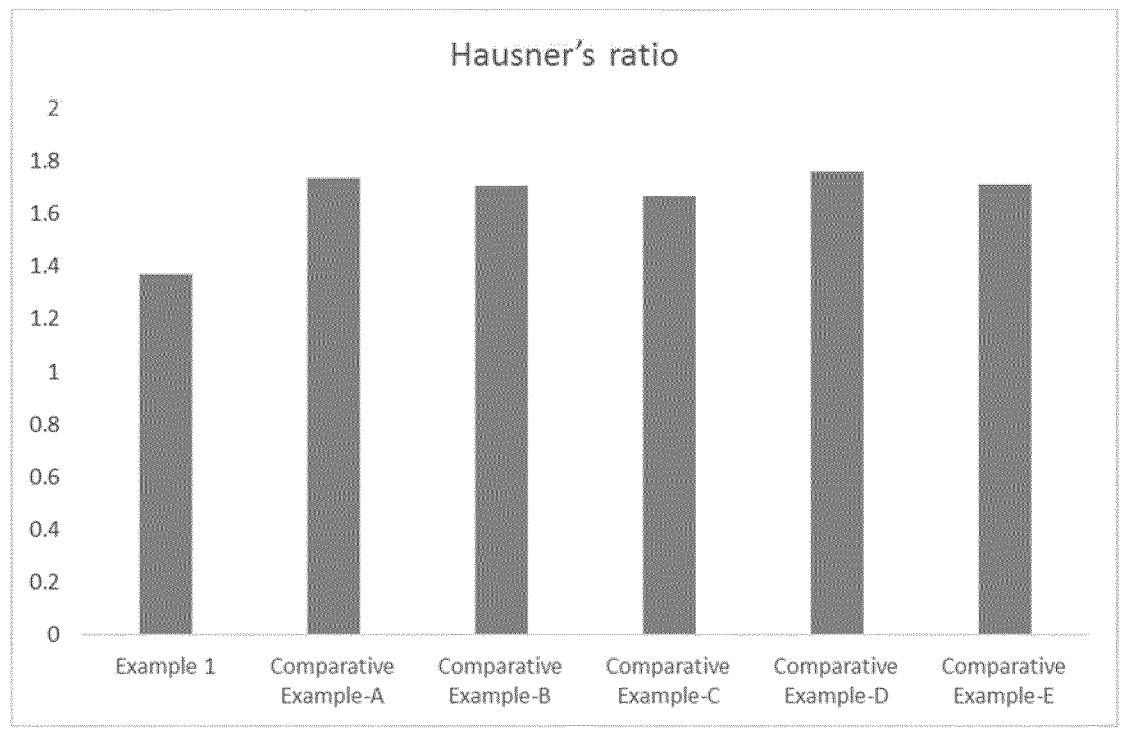

FIG. 2 compares the Hausner Ratio of the formulations of Example 1 and Comparative Examples A-E.

Figure 3:
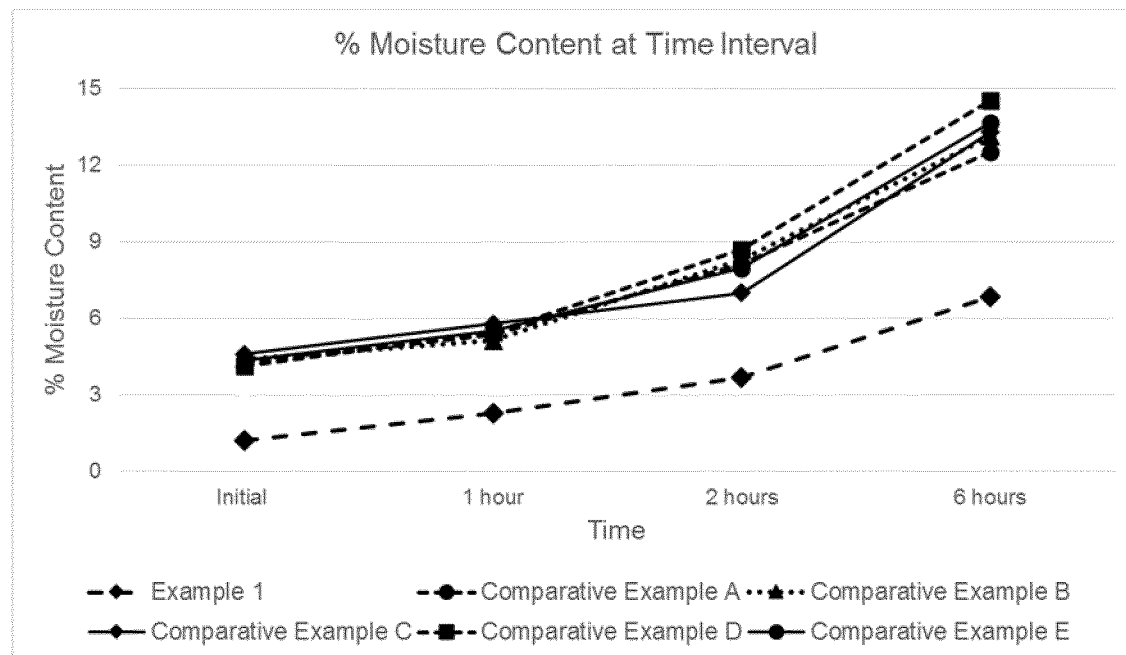

FIG. 3 depicts the % Moisture Content of the formulations of Example 1 and Comparative Examples A-E as a function of storage time.

Figure 4:
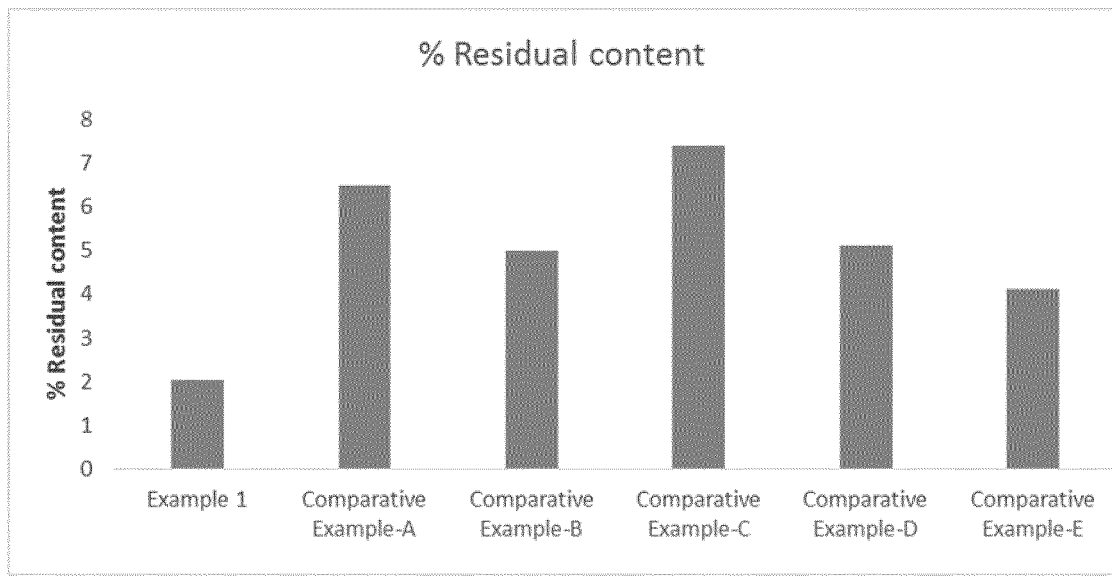

FIG. 4 compares the % Residual Content of the formulations of Example 1 and Comparative Examples A-E.

Figure 5:
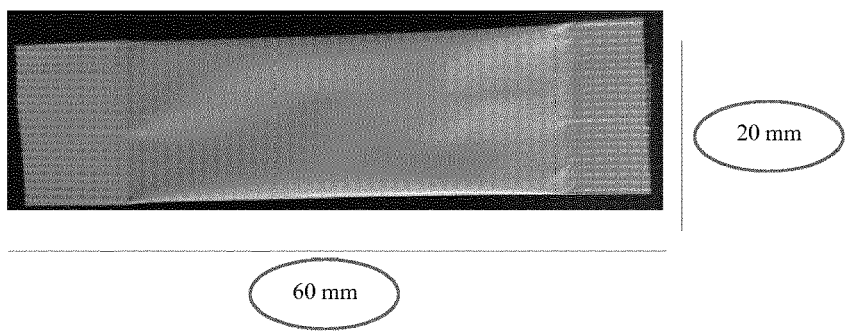

FIG. 5 is a photograph of a stick pack of the invention.

Figure 6:
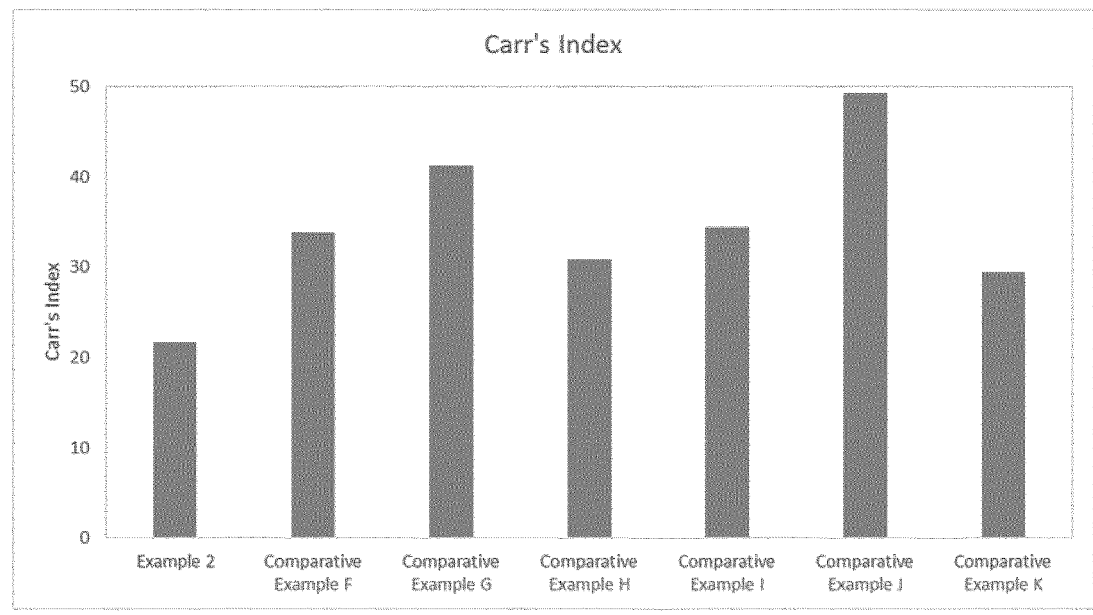

FIG. 6 compares the Compressibility Index (Carr Index) of the formulations of Example 2 and Comparative Examples F-K.

Figure 7:
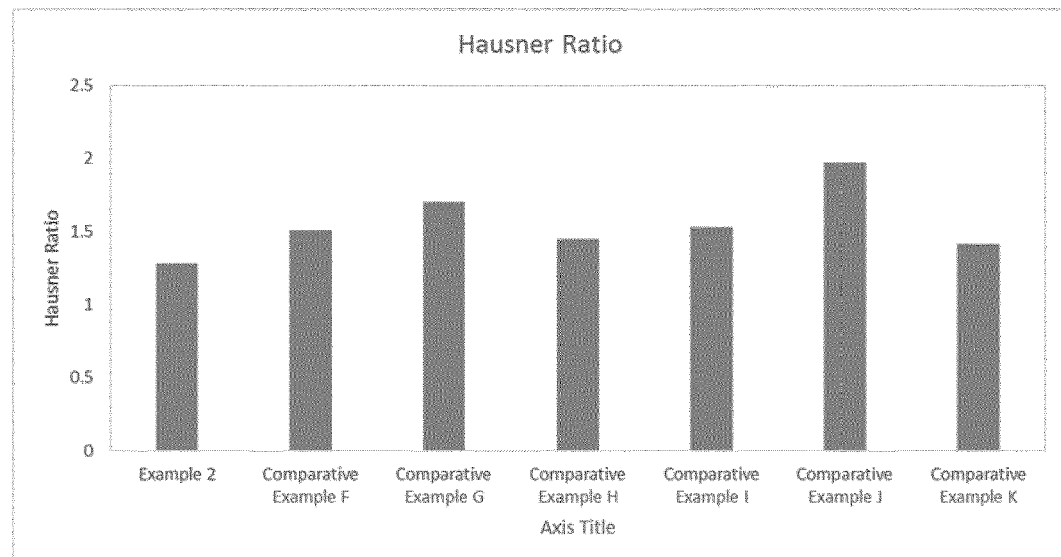

FIG. 7 compares the Hausner Ratio of the formulations of Example 2 and Comparative Examples F-K.

Figure 8:
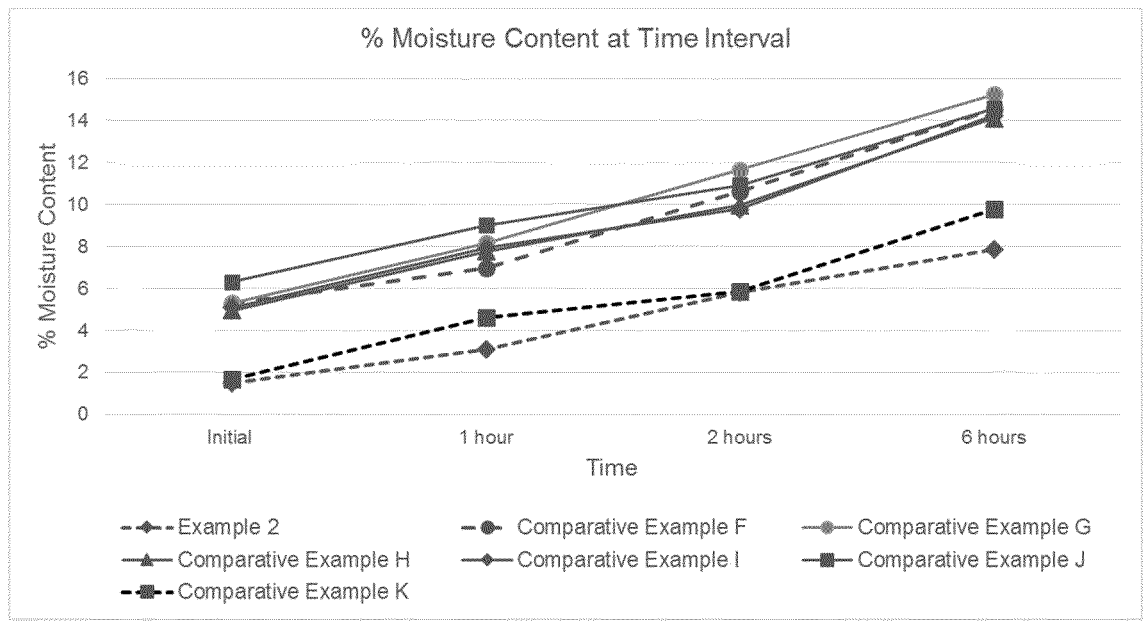

FIG. 8 depicts the % Moisture Content of the formulations of Example 2 and Comparative Examples F-K as function of storage time.

Figure 9:
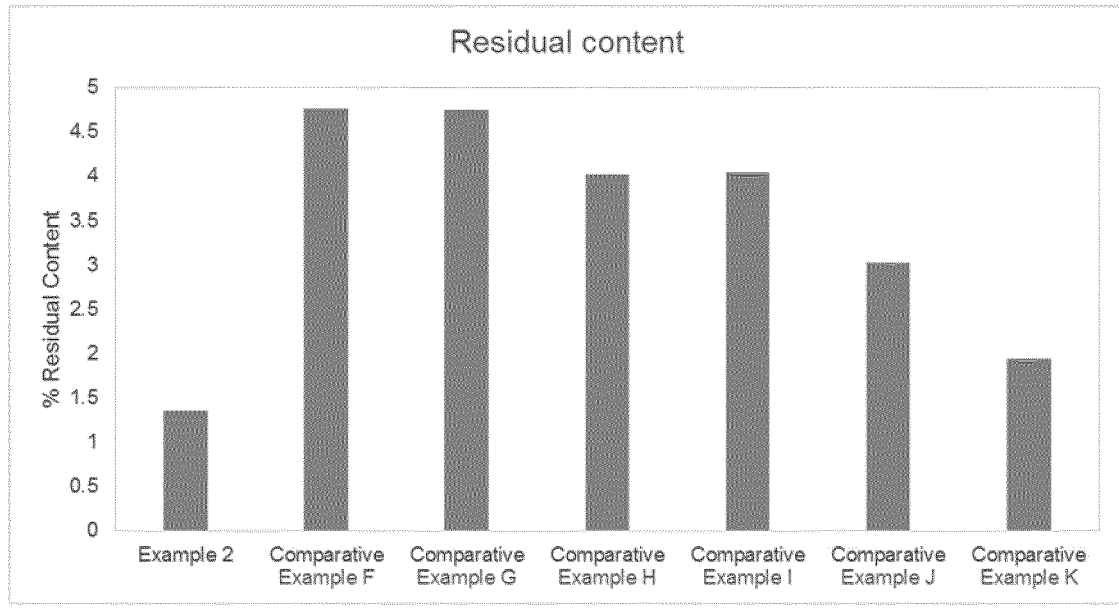

FIG. 9 compares the % Residual Content of the formulations of Example 2 and Comparative Examples F-K.

Figure 10:
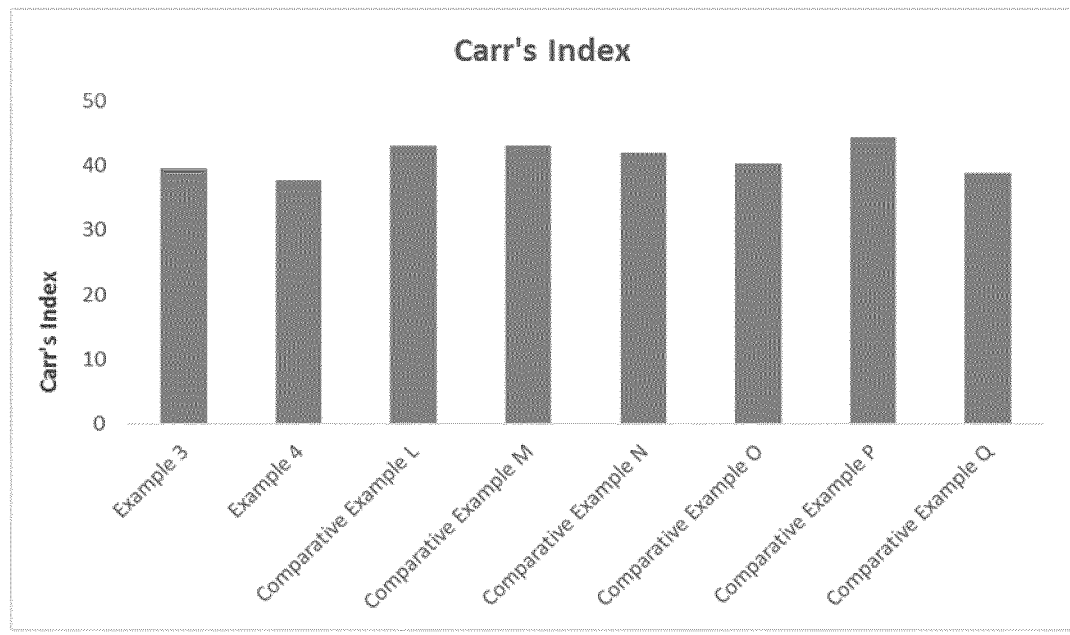

FIG. 10 compares the Compressibility Index (Carr Index) of the formulations of Example 3-4 and Comparative Examples L-Q.

Figure 11:
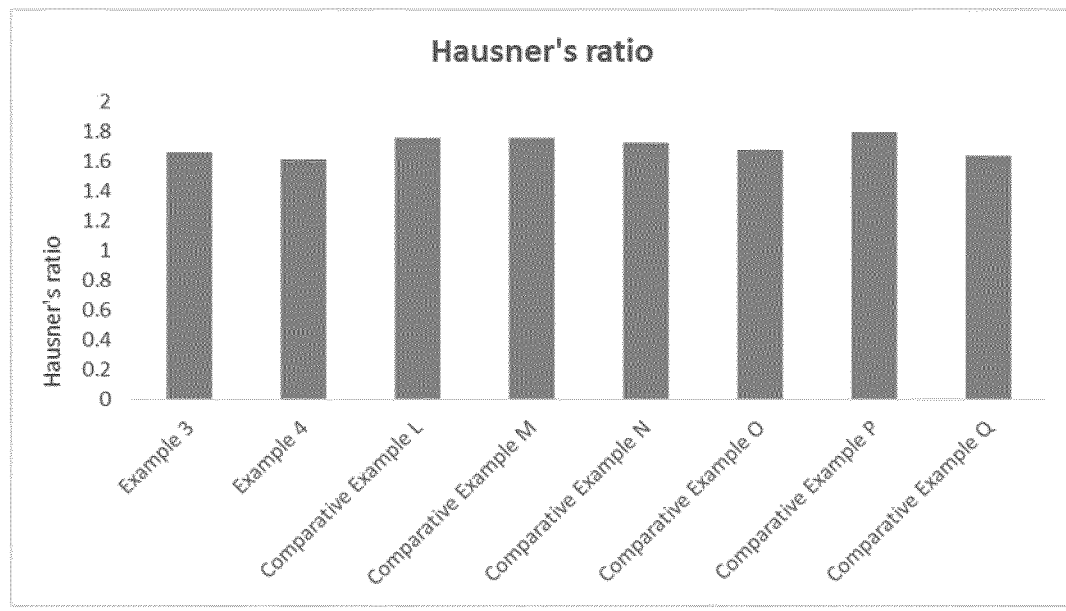

FIG. 11 compares the Hausner Ratio of the formulations of Example 3-4 and Comparative Examples L-Q.

Figure 12:
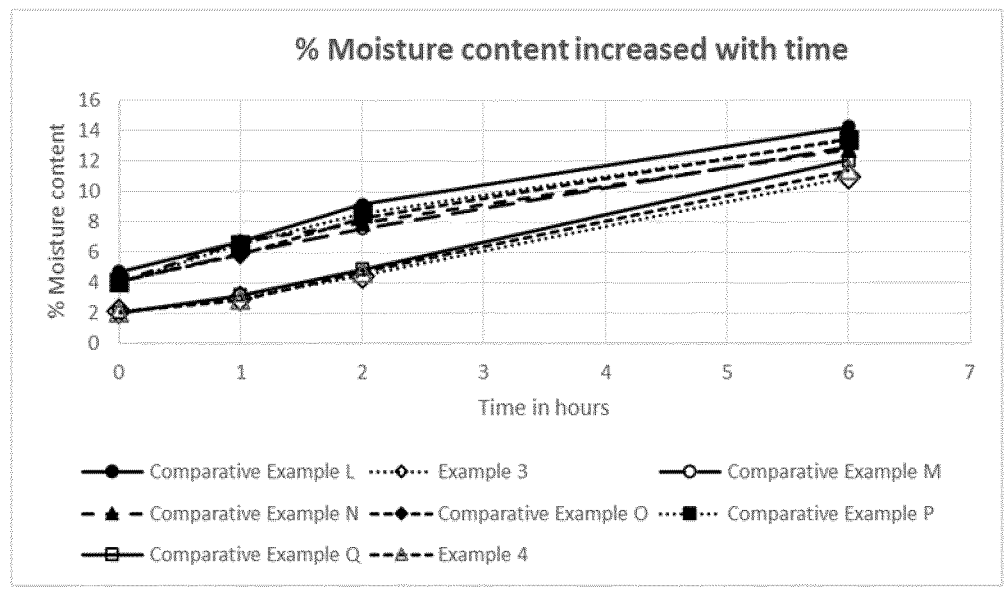

FIG. 12 depicts the % Moisture Content of the formulations of Example 3-4 and Comparative Examples L-Q as function of storage time.

Figure 13:
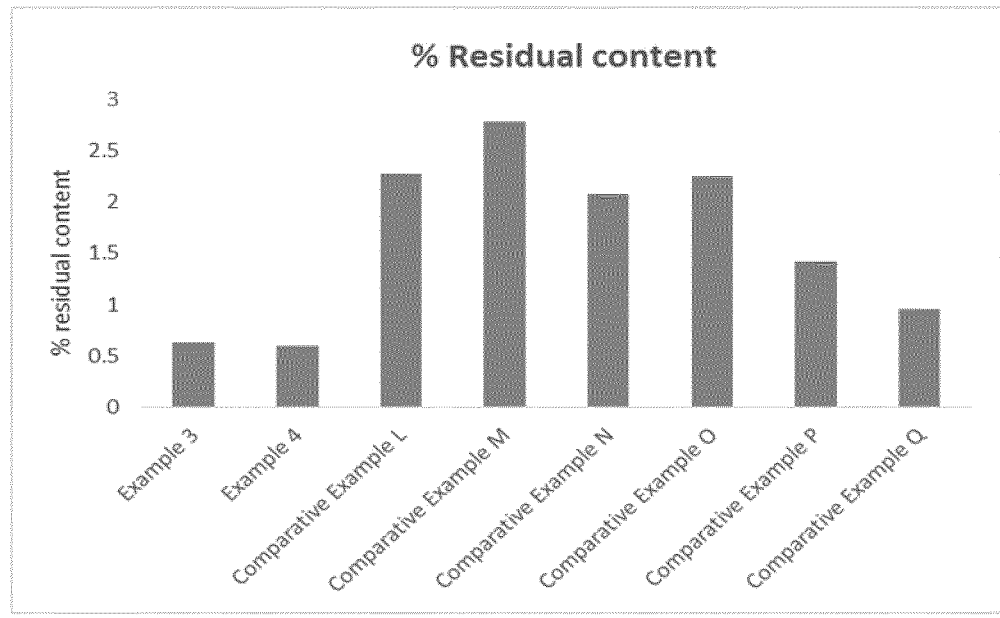
Figure 14:
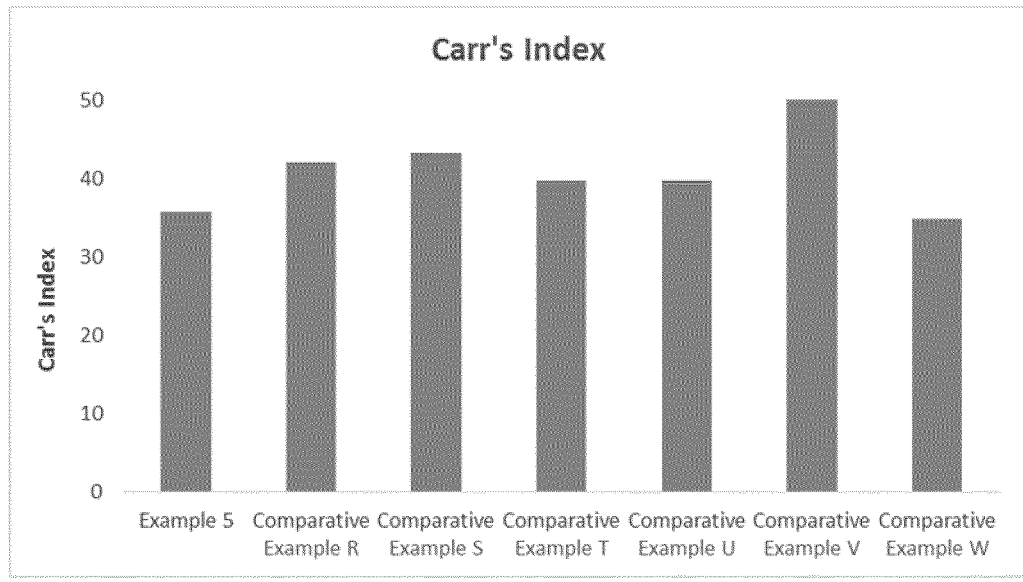

FIG. 13 compares the % Residual Content of the formulations of Example 3-4 and Comparative Examples L-Q FIG. 14 compares the Compressibility Index (Carr Index) of the formulations of Example 5 and Comparative Examples R-W.

Figure 15:
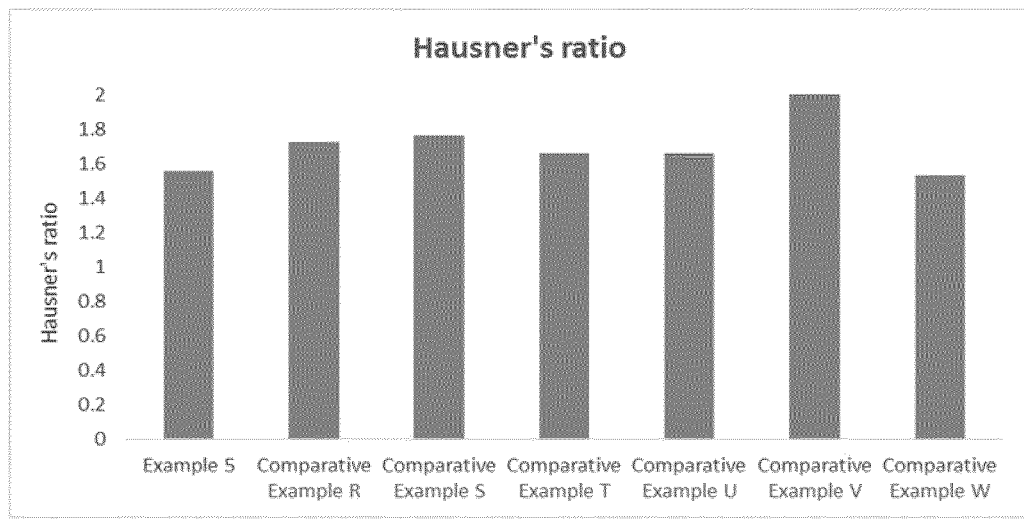

FIG. 15 compares the Hausner Ratio of the formulations of Example 5 and Comparative Examples R-W.

Figure 16:
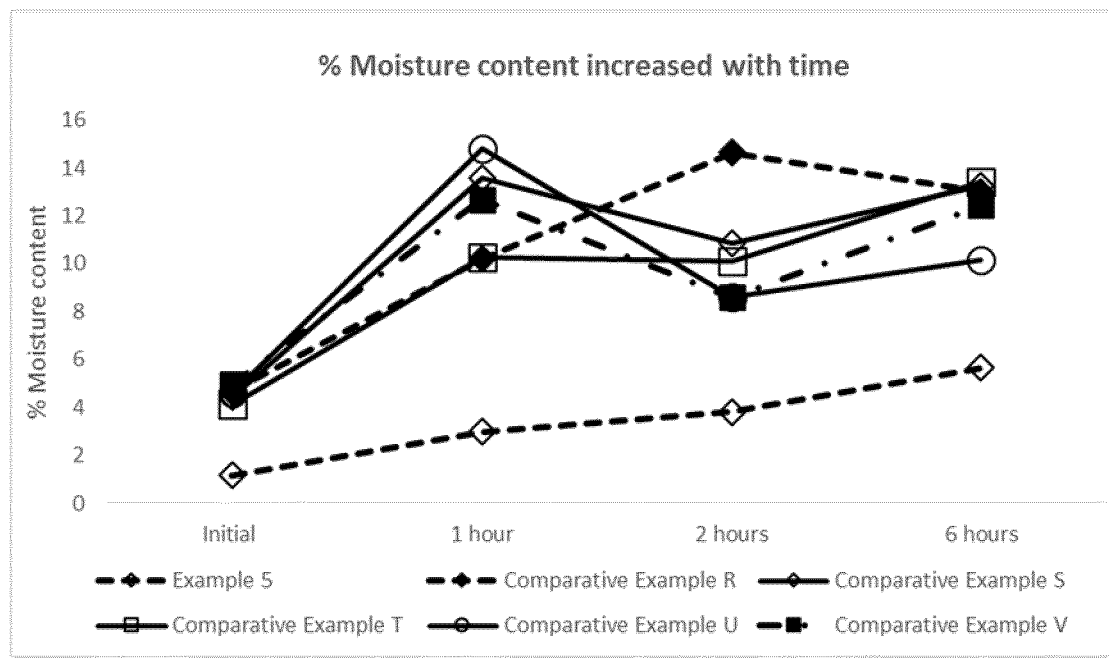

FIG. 16 depicts the % Moisture Content of the formulations of Example 5 and Comparative Examples R-W as function of storage time.

Figure 17:
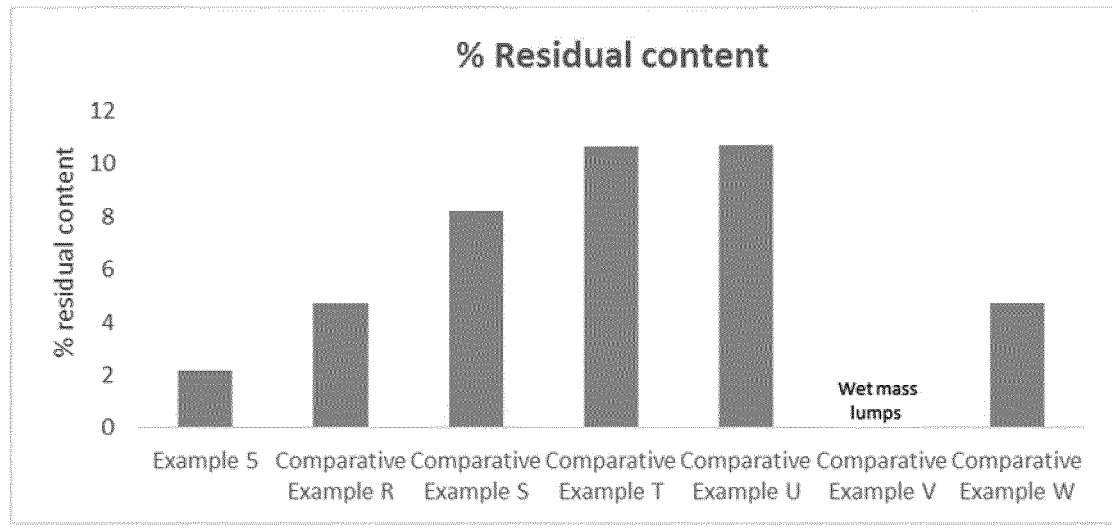

FIG. 17 compares the % Residual Content of the formulations of Example 5 and Comparative Examples R-W

DETAILED DESCRIPTION OF THE INVENTION

The present invention provides a novel blend composition of sorbitol and liquid paraffin for use in the improvement of formulation properties of pharmaceutical formulations in several parameters, i.e. flow properties, moisture protection, antistatic properties and compressibility. The blend composition may also contain citric acid and has ability to mitigate the taste of bitter drugs.

The novel blend, when mixed with lyophilized powder, provides a pharmaceutical formulation with improved properties, e.g., flow properties, moisture protection, antistatic properties and compressibility.

The present invention thus provides a free-flowing solid pharmaceutical formulation comprising one or more active ingredients and a blend composition comprising or consisting of sorbitol, liquid paraffin and optionally citric acid.

The formulation preferably comprises 0.01% to 30% by weight of one or more active ingredients, 70% to 99.99% by weight of the blend composition, and 0% to 30% by weight of one or more other pharmaceutically acceptable excipients. More preferably, the formulation comprises 0.1% to 28% by weight of one or more active ingredients, 72% to 99.9% by weight of the blend composition, and 5% to 30% by weight of one or more other pharmaceutically acceptable excipients. In an embodiment of the invention, the formulation is obtained by a process including steps of forming the blend composition by blending sorbitol, liquid paraffin and optionally citric acid, and adding the blend composition to the active ingredient(s), which is preferably a lyophilized powder.

The present invention further provides a blend composition comprising or consisting of sorbitol, liquid paraffin and optionally citric acid for use in the manufacture of a pharmaceutical formulation comprising one or more active ingredients. The blend composition preferably comprises 95 to 99.9% by weight of sorbitol, 0.1% to 5% by weight of liquid paraffin, and 0 to 4% by weight of citric acid. More preferably, the blend composition comprises 96 to 99.5% by weight of sorbitol, 0.5% to 4% by weight of liquid paraffin, and 0.5 to 2% by weight of citric acid. In one embodiment, the blend composition consists of the indicated components, in the indicated preferred and more preferred proportions.

The present invention also provides a process for the manufacture of a solid pharmaceutical formulation of the invention comprising:
(a) forming a lyophilized powder by subliming the solvent from a preparation comprising one or more active ingredients and the solvent;
(b) forming a blend composition comprising or consisting of sorbitol, liquid paraffin and optionally citric acid;
(c) mixing the blend composition obtained in step (b) with the lyophilized powder obtained in step (a).

The process of the invention allows obtaining a solid pharmaceutical formulation in the form of a free-flowing powder.

Preferred proportions of active ingredient(s), sorbitol, liquid paraffin, citric acid and blend composition in the process of the present invention are the same as in the pharmaceutical formulation of the present invention.

The solvent used in the preparation to be lyophilized, comprising active ingredient(s) and solvent, typically is water.

The terms "active ingredient" and "pharmaceutically active ingredient" are used interchangeably herein.

The pharmaceutical formulation of the present invention comprises one or more pharmaceutically active ingredients. They may be selected from, e.g., oligopeptides, polypeptides (proteins), nucleotides, polynucleotides and "small molecules". Non-limiting examples of pharmaceutically active ingredients which can be used in the present invention are analgesics, alpha blockers, anti-allergy agents, anti-asthma agents, anti-rhinitis agents, anti-uticaria agents, anti-inflammatory agents, anti-arrhythmic agents, anti-bacterial agents, anti-psychotics, anti-diabetics, anti-diuretics, anti-epileptics, anti-fungal agents, anti-gout agents, anti-hypertensive agents, anti-incontinence agents, anti-migraine agents, anti-muscarinic agents and immunosuppressants, antivirals, anxiolytics, sedatives, hypnotics and neuroleptics, anti-benign hyperplasia (BPH agents), decongestants, diuretics, enzymes, anti-parkinsonian agents, gastro-intestinal agents, histamine receptor antagonists, infertility agents, endometriosis agents, hormone replacement therapy agents, lipid regulating agents, local anesthetics, neuromuscular agents, motion sickness agents, nutritional agents, oral vaccines, proteins, peptides and recombinant drugs, proton pump inhibitors, anti-schizophrenia agents, hormones, contraceptives, seizure/panic disorder agents, sexual dysfunction (male and female) agents and so forth.

Specific non-limiting examples of these active ingredients are:
Anti-allergics: desloratadine, loratadine, Montelukast, Montelukast sodium, Cetirizin, Fexofenadin, Ebastine.
Alfa blockers: Tamsulosin, Silodosin Analgesics and anti-inflammatory agents: aspirin, aloxiprin, auranofin, azapropazone, benorylate, diflunisal, etodolac, fenbufen, fenoprofen calcium, flurbiprofen, ibuprofen, indomethacin, ketoprofen, meclofenamic acid, mefenamic acid, nabumetone, naproxen, oxaprozin, oxyphenbutazone, phenylbutazone, piroxicam, sulindac, paracetamol.
Anti-arrhythmic agents: amiodarone HCl, disopyramide, flecainide acetate, quinidine sulphate.
Anti-bacterial agents: benethamine penicillin, cinoxacin, ciprofloxacin HCl, clarithromycin, do fazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim.
Anti-psychotics: amoxapine, ciclazindol, maprotiline HCl, mianserin HCl, nortriptyline HCl, trazodone HCl, trimipramine maleate.
Anti-diabetics: acetohexamide, chlorpropamide, glibenclamide, gliclazide, glipizide, tolazamide, tolbutamide.
Anti-diuretics: desmopressin and its analog, desmopressin acetate.
Anti-epileptics: beclamide, carbamazepine, clonazepam, ethotoin, methoin, methsuximide, methylphenobarbitone, oxcarbazepine, paramethadione, phenacemide, phenobarbitone, phenytoin, phensuximide, primidone, sulthiame, valproic acid.
Anti-fungal agents: amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid.
Anti-gout agents: allopurinol, probenecid, sulphinpyrazone.
Anti-hypertensive agents: amlopidine, benidipine, darodipine, dilitazem HCl, diazoxide, felodipine, guanabenz acetate, indoramin, isradipine, minoxidil, nicardipine HCl, nifedipine, nimodipine, phenoxybenzamine HCl, prazosin HCl, reserpine, terazosin HCl.
Anti-migraine agents: rizatriptan, dihydroergotamine mesylate, ergotamine tartrate, methysergide maleate, pizotifen maleate, sumatriptan succinate, caffeine.
Anti-muscarinic agents: oxybutinin, tolterodin, atropine, benzhexol HCl, biperiden, ethopropazine HCl, hyoscine butyl bromide, hyoscyamine, mepenzolate bromide, orphenadrine, oxyphencylcimine HCl, tropicamide.
Anti-rhinitis agents, anti-uticaria agents: Cetirizin, fexofenadin, ebastine, loratadine, montelukast.
Antivirals: acyclovir, amantadine hydrochloride, famciclovir, zidovadine, didanosine, zalcitabine, foscarnet sodium.
Anxiolytic agents, sedatives, hypnotics and neuroleptics: alprazolam, amylobarbitone, barbitone, bentazepam, bromazepam, bromperidol, brotizolam, butobarbitone, carbromal, chlordiazepoxide, Chlorpheniramine, chlormethiazole, chlorpromazine, clobazam, clonazepan, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine phenylephrine, pimozide, prochlorperazine, pseudoephedrineHCL, sulpride, temazepam, thioridazine, triazolam, zopiclone.

Contraceptives: clomiphene citrate, danazol, desogestrel, ethinyloestradiol, ethynodiol, ethynodiol diacetate, levonorgestrel, medroxyprogesterone acetate, mestranol, methyltestosterone, norethisterone, norethisterone enanthate, norgestrel, estradiol, conjugated estrogens, dydrogesterone, progesterone, stanozolol, stilboestrol, testosterone, tibolone.

Decongestants: pseudoephedrine hydrochloride.

Diuretics: acetazolamide, amiloride, bendrofluazide, bumetanide, chlorothiazide, chlorthalidone, ethacrynic acid, frusemide, metolazone, spironolactone, triamterene.

Enzymes: pancreatin, pepsin, lipase.

Epilepsy: Gabapentin

Anti-parkinsonian agents: bromocriptine mesylate, lysuride maleate, selegiline, para-fluoroselegiline, lazabemide, rasagiline, 2-BUMP [N-(2-butyl)-N-methylpropargylamine], M-2-PP [N-methyl-N-(2-pentyl)-propargylamine], MDL-72145 [beta-(fluoromethylene)-3,4-dimethoxy-benzeneethanamine], mofegiline, apomorphine, N-propylnoraporphine, cabergoline, metergoline, naxagolide, pergolide, piribedil, ropinirole, terguride, quinagolide.

Gastro-intestinal agents: bisacodyl, cimetidine, cisapride, diphenoxylate HCl, domperidone, metoclopramide, famotidine, loperamide, mesalazine, nizatidine, esomeprazole, metopimazine, pantoprazole, ondansetron HCl, Granisetron, tropisetron, dolasetron, ranitidine HCl, sulphasalazine. Lanzoprazole.

Histamine Receptor Antagonists: acrivastine, astemizole, cinnarizine, cyclizine, cyproheptadine HCl, dimenhydrinate, flunarizine HCl, loratadine, meclozine HCl, oxatomide, terfenadine, triprolidine.

Hormones: Human Growth hormone (HGH), Follicle Stimulating Hormone (FSH), Gonadotropin-releasing hormone (GnRH) agonists or antagonists, nafarelin Triptorelin, cetrorelix, atosiban.

Hormone replacement therapy agents: dydrogesterone.

Anti-hypertension agents: Enalapril.

Lactation agents: Oxytocin, oxytocin agonists.

Lipid regulating agents: bezafibrate, clofibrate, fenofibrate, gemfibrozil, probucol.

Local anaesthetics: amethocaine, amylocaine, benzocaine, bucricaine, bupivacaine, butacaine, butanilicaine, butoxycaine, butyl aminobenzoate, carticaine, chloroprocaine, cinchocaine, clibucaine, clormecaine, coca, cocaine, cyclomethycaine, dimethisoquin, diperodon, dyclocaine, ethyl chloride, ethyl p-piperidinoacetylaminobenzoate, etidocaine, hexylcaine, isobutamben, ketocaine, lignocaine, mepivacaine, mepryl-caine, myrtecaine, octacaine, oxethazaine, oxybuprocaine, parethoxycaine, pramoxine, prilocaine, procaine, propranocaine, propoxycaine, proxymetacaine, ropivacaine, tolycaine, tricaine, trimecaine, vadocaine.

Motion sickness agents: diphenhydramine.

Neuro-muscular agents: pyridostigmine.

Nonsteroidal antiandrogens: Enzalutamide.

Nutritional agents: betacarotene, vitamins, such as vitamin A, vitamin $B_2$, vitamin D, vitamin E, vitamin K, minerals.

Oral vaccines: to prevent or reduce the symptoms of diseases such as Influenza, Tuberculosis, Meningitis, Hepatitis, Whooping Cough, Polio, Tetanus, Diphtheria, Malaria, Cholera, Herpes, Typhoid, HIV, AIDS, Measles, Lyme disease, Traveller's Diarrhea, Hepatitis A, B and C, Otitis Media, Dengue Fever, Rabies, Parainfluenza, Rubella, Yellow Fever, Dysentery, Legionnaires Disease, Toxoplasmosis, Q-Fever, Haemorrhegic Fever, Argentina Haemorrhegic Fever, Caries, Chagas Disease, Urinary Tract Infection caused by *E. coli*, Pneumococcal Disease, Mumps, Chikungunya, Hay fever, Asthma, Rheumatoid Arthritis, Carcinomas, Coccidiosis, Newcastle Disease, Enzootic pneumonia, Feline leukemia, Atrophic rhinitis, Erysipelas, Foot and Mouth disease and Swine pneumonia, or to prevent or reduce the symptoms of diseases caused by *Vibrio* species, *Salmonella* species, *Bordetella* species, *Haemophilus* species, Toxoplasmosis *gondii*, Cytomegalovirus, *Chlamydia* species, Streptococcal species, Norwalk Virus, *Escherischia coli, Helicobacter pylori, Rotavirus, Neisseria gonorrhae, Neisseria meningiditis*, Adenovirus, Epstein Barr Virus, Japanese Encephalitis Virus, *Pneumocystis carini*, Herpes simplex, Clostridia species, Respiratory Syncytial Virus, *Klebsiella* species, *Shigella* species, *Pseudomonas aeruginosa*, Parvovirus, *Campylobacter* species, *Rickettsia* species, Varicella zoster, *Yersinia* species, Ross River Virus, J. C. Virus, *Rhodococcus equi, Moraxella catarrhalis, Borrelia burgdorferi* and *Pasteurella haemolytica*, BCG.

Agents for voiding dysfunctions: Tamsulosin, trospium chloride, tolterodine, oxybutynin, Solifenacin.

Proteins, peptides and recombinant drugs: recombinant hormones and iso-hormones, recombinant cytokines, recombinant plasminogens, TNF receptor fusion protein, monoclonal antibodies, nucleic acids, antisense oligonucleotides, oligonucleotides, glycoproteins and adhesion molecules, Calcitonin, octreotide, insulin and insulin analogs, etanercept, pegfilgrastim, liraglutide, bivalirudin, nesiritide, ceruletide, bentiromide, exenatide, gonadorelin, enfuvirtide, vancomycin, icatibant, secretin, leuprolide, glucagon recombinant, oxytocin, sermorelin, gramicidin D, Insulin recombinant, capreomycin, vasopressin, cosyntropin, bacitracin, abarelix, vapreotide, thymalfasin, mecasermin, teriparatide, corticotropin, pramlintide.

Phosphate Binders: Sevelamer.

Sexual dysfunction agents: Cabergolin, oxytocin, tadalafil, sildenafil, vardenafil.

Stimulants: amphetamine, dexamphetamine, dexfenfluramine, fenfluramine.

In a specific embodiment, the active ingredient of a formulation of the invention is selected from the group consisting of desloratadine, montelukast, solifenacin, silodosin, sildenafil and any pharmaceutically acceptable salt thereof.

In a specific embodiment, the active ingredient of a formulation of the invention is desloratadine.

In a specific embodiment, the active ingredient of a formulation of the invention is sildenafil.

In a specific embodiment, the active ingredient of a formulation of the invention is solifenacin.

In addition to the components discussed above, the formulation may also include other excipients (auxiliary agents, accessory agents) such as, but not limited to fillers, thickeners (including but not limited to guar gum and xanthan gum), binders, diluents, lubricants, pH adjusting agents, protecting agents, viscosity enhancers, wicking agents, non-effervescent disintegrants, effervescent disintegrants, surfactants, anti-oxidants, wetting agents, colorants, flavoring agents, taste-masking agents, sweeteners, preservatives and so forth.

A suitable route of administration for a dosage form of the present invention is oral administration.

In one embodiment, a pharmaceutical formulation of the invention can be administered to a patient in the form of a powder.

In another aspect, a pharmaceutical formulation of the invention is contained in a package dispensing single doses of the formulation, also named a unit dosage form. Non-limiting examples of a package/unit dosage form are a sachet and a stick pack.

In another embodiment, a pharmaceutical formulation of the invention, e.g., in the form of a powder, is packed in a multi-dosage form, i.e. a dosage form allowing withdrawing multiple doses of arbitrary size. Non-limiting examples of a multi-dosage form are a bottle and any other container capable of holding a powder.

A patient administered with a free-flowing powder formulation of the invention will be certain that he receives the entire dosage, i.e. there will be no residue left in the package/unit dosage form.

In one embodiment, the oral administration is carried out by emptying a sachet, stick pack or (any other) unit pack containing the powder onto the tongue and swallowing the content.

In another embodiment, the oral administration is carried out by dissolving the powder in a solvent (e.g. a glass of water) and then drink the solution.

The exact dose and regimen of administration of the dosage form will necessarily depend upon the therapeutic effect to be achieved and may vary with the particular active ingredient, the route of administration, and the age and condition of the individual subject to whom the formulation is to be administered. At times patients may be instructed to take two or any other number of unit dosage forms, e.g. stick packs, in a single administration or at times only a portion, such as half or a quarter, of the unit dosage form in a single administration.

The formulations of the invention are unique in that they have improved flow properties, moisture content, antistatic properties and compressibility.

The pharmaceutical formulation of the invention may be obtained by:
(a) forming a lyophilized powder by subliming the solvent (e.g. water), for example in a freeze drying process, from a preparation that comprises the active ingredient(s) and the solvent;
(b) forming a blend composition comprising sorbitol and liquid paraffin. The blend composition may optionally contain citric acid;
(c) mixing the blend composition with the lyophilized powder obtained in step (a) to obtain a pharmaceutical composition with improved flow properties, moisture protection, antistatic properties and compressibility.

According to one embodiment, the resulting free flowing composition is introduced into a stick pack.

According to another embodiment, the resulting free flowing composition is introduced into a sachet.

The free flowing blend composition of sorbitol and liquid paraffin is mixed with a lyophilized powder by methods known in the art such as geometric mixing or mixing with any type of blender.

EXAMPLES

The invention is further described in the following examples, which are not in any way intended to limit the scope of the inventions as claimed.

Materials and Methods

| Material | Manufactured by | Supplied by |
| --- | --- | --- |
| Polacrillin Potassium (resin) | Dow France S.A.S | Colorcon India |
| Malto dextrin | Roquette France | Signet India |
| Citric acid | Merck | Merck |
| Talc | Imerys Talc | Signet India |
| Magnesium stearate | Sun-shine | Sun-shine |
| Liquid paraffin | Ashwini chemicals pvt. Ltd. | Ashwini chemicals pvt. Ltd. |
| Sorbitol | Roquette | Signet India |
| Desloratadine | Enaltec | Enaltec |
| Sodium Hydroxide | Merck | Merck |
| Mannitol | Roquette France | Signet India |
| Hydroxypropyl cellulose L | Ashland | Ashland |
| Tartaric acid pellets | Ideal cures | Ideal cures |
| Sildenafil citrate | Rakshit drugs | Rakshit drugs |
| Solifenacin | MSN Lab | MSN Lab |

Example 1: Placebo Formulation

A (placebo) formulation was prepared using the following ingredients:

| | Ingredients | Quantity per 1000 Stick Packs (g) |
| --- | --- | --- |
| Lyophilized Granules prepared from liquid composition composed of: | | |
| 1 | Resin | 20.0 |
| 2 | Malto dextrin | 77.0 |
| 3 | Citric acid | 3.0 |
| 4 | Water | q.s. to 400 g |
| Blend Composition | | |
| 5 | Sorbitol | 394.5 |
| 6 | Citric acid | 3.0 |
| 7 | Liquid paraffin | 2.5 |

Manufacturing Procedure:
I. Lyophilized Granules
1. Citric acid was dissolved in 200 g of water using a magnetic/overhead stirrer for 5 minutes.
2. Resin was added under continuous stirring and the dispersion formed was kept under stirring for 1 hour.
3. Maltodextrin was added under continuous stirring.
4. The final weight of the solution/dispersion was made to 400 g using purified water.
5. Mixing of the solution/dispersion was continued for 10 minutes in a magnetic/overhead stirrer.
6. This solution/dispersion was filled in stainless steel tray and freeze-dried in a lyophilizer.
7. After complete freeze drying, the lyophilized cake was sieved through a #40 sieve to obtain the lyophilized granules.
II. Blend Composition
8. Sorbitol was passed through a #40 sieve and mixed with crushed and sieved citric acid in a double cone blender for 2 minutes at 10 RPM.
9. Liquid paraffin was added dropwise to 40 g of the mixture from step 8, and mixed manually to obtain a uniformly distributed blend composition.
10. The blend composition was sieved through a #60 sieve and then mixed with remaining mixture from step 8 using a double cone blender for 3 minutes at 10 RPM to obtain the final blend composition.

III. Formulation
  11. The lyophilized granules from step 7 were mixed with the final blend composition from step 10 in a double cone blender for 5 minutes at 10 RPM to obtain the free flowing (placebo) composition.
  12. The free flowing composition was filled into stick packs and sealed, at 500 mg per stick pack (see FIG. 5).

Example 2: Desloratadine Composition

A formulation of desloratadine was prepared using the following ingredients:

| Ingredients | Quantity per 1000 Stick Packs (g) |
|---|---|
| Lyophilized Granules prepared from liquid composition composed of: | |
| 1 Desloratadine | 10.0 |
| 2 Resin | 20.0 |
| 3 Malto dextrin | 67.0 |
| 4 Citric acid | 3.0 |
| 5 Water | q.s. to 400 g |
| Blend Composition | |
| 6 Sorbitol | 394.5 |
| 7 Citric acid | 3.0 |
| 8 Liquid paraffin | 2.5 |

Manufacturing Procedure
I. Lyophilized Granules
  1. Citric acid was dissolved in 200 g of water using a magnetic/overhead stirrer for 5 minutes.
  2. Desloratadine was added under continuous stirring using a magnetic/overhead stirrer.
  3. Resin was added under continuous stirring and the dispersion formed was kept under stirring for 1 hour.
  4. Maltodextrin was added under continuous stirring.
  5. The final weight of the solution/dispersion was made to 400 g using purified water.
  6. Mixing of the solution/dispersion was continued for 10 minutes in a magnetic/overhead stirrer.
  7. This solution/dispersion was filled in stainless steel tray and freeze-dried in a lyophilizer.
  8. After complete freeze drying, the lyophilized cake was sieved through a #40 sieve to obtain the lyophilized granules.
II. Blend Composition
  9. Sorbitol was passed through a #40 sieve and mixed with crushed and sieved citric acid in a double cone blender for 2 minutes at 10 RPM.
  10. Liquid paraffin was added dropwise to 40 g of the mixture from step 9, and mixed manually to obtain a uniformly distributed blend composition.
  11. The blend composition was sieved through a #60 sieve and then mixed with remaining mixture from step 9 using a double cone blender for 3 minutes at 10 RPM to obtain the final blend composition.
III. Formulation
  12. The lyophilized granules from step 8 were mixed with the final blend composition from step 11 in a double cone blender for 5 minutes at 10 RPM to obtain the free flowing desloratadine formulation.
  13. The free flowing composition was filled into stick packs and sealed, at 500 mg per stick pack (see FIG. 5).

Comparative Example A

A granule formulation was prepared essentially as described in Example 1 using the following ingredients:

| Ingredients | Quantity per 1000 Stick Packs (g) |
|---|---|
| 1 Resin | 33.0 |
| 2 Malto dextrin | 129.0 |
| 3 Citric acid | 8.0 |
| 4 Water | q.s. to 200 g |

Comparative Example B

A comparative pharmaceutical formulation was prepared essentially as described in Example 1 by using a blend composition containing talc and the other following ingredients:

| Ingredients | Quantity per 1000 Stick Packs (g) |
|---|---|
| Lyophilized Granules prepared from liquid composition composed of: | |
| 1 Resin | 33.0 |
| 2 Malto dextrin | 127.0 |
| 3 Citric acid | 5.0 |
| 4 Water | q.s. to 200 g |
| Blend Composition | |
| 5 Citric acid | 3.0 |
| 6 Talc | 2.5 |

Comparative Example C

A comparative pharmaceutical formulation was prepared essentially as described in Example 1 by using a blend composition containing Magnesium stearate and the other following ingredients:

| Ingredients | Quantity per 1000 Stick Packs (g) |
|---|---|
| Lyophilized Granules prepared from liquid composition composed of: | |
| 1 Resin | 33.0 |
| 2 Malto dextrin | 127.0 |
| 3 Citric acid | 5.0 |
| 4 Water | q.s. to 200 g |
| Blend Composition | |
| 5 Citric acid | 3.0 |
| 6 Magnesium stearate | 2.5 |

Comparative Example D

A comparative pharmaceutical formulation was prepared essentially as described in Example 1 by using a blend composition containing Talc, Magnesium stearate and the other following ingredients:

| Ingredients | Quantity per 1000 Stick Packs (g) |
|---|---|
| Lyophilized Granules prepared from liquid composition composed of: | |
| 1 Resin | 33.0 |
| 2 Malto dextrin | 127.0 |
| 3 Citric acid | 5.0 |
| 4 Water | q.s. to 200 g |

-continued

| | Ingredients | Quantity per 1000 Stick Packs (g) |
|---|---|---|
| | Blend Composition | |
| 5 | Citric acid | 3.0 |
| 6 | Talc | 1.3 |
| 7 | Magnesium stearate | 1.3 |

Comparative Example E

A comparative pharmaceutical formulation was prepared essentially as described in Example 1 by using a blend composition containing only liquid paraffin and the other following ingredients:

| | Ingredients | Quantity per 1000 Stick Packs (g) |
|---|---|---|
| | Lyophilized Granules prepared from liquid composition composed of: | |
| 1 | Resin | 33.0 |
| 2 | Malto dextrin | 127.0 |
| 3 | Citric acid | 5.0 |
| 4 | Water | q.s. to 200 g |
| | Blend Composition | |
| 5 | Citric acid | 3.0 |
| 6 | Liquid paraffin | 2.5 |

Comparative Example F

A granule formulation was prepared essentially as described in Example 2 using the following ingredients:

| | Ingredients | Quantity per 1000 Stick Packs (g) |
|---|---|---|
| 1 | Desloratadine | 16.7 |
| 2 | Resin | 33.40 |
| 3 | Malto dextrin | 111.89 |
| 4 | Citric acid | 8.0 |
| 5 | Water | q.s. to 668 g |

Comparative Example G

A comparative pharmaceutical formulation was prepared essentially as described in Example 2 by using a blend composition containing talc and the other following ingredients:

| | Ingredients | Quantity per 1000 Stick Packs (g) |
|---|---|---|
| | Lyophilized Granules prepared from liquid composition composed of: | |
| 1 | Desloratadine | 16.45 |
| 2 | Resin | 33.0 |
| 3 | Malto dextrin | 110.0 |
| 4 | Citric acid | 5.0 |
| 5 | Water | q.s. to 658 g |
| | Blend Composition | |
| 6 | Citric acid | 3.0 |
| 7 | Talc | 2.5 |

Comparative Example H

A comparative pharmaceutical formulation was prepared essentially as described in Example 2 by using a blend composition containing Magnesium stearate and the other following ingredients:

| | Ingredients | Quantity per 1000 Stick Packs (g) |
|---|---|---|
| | Lyophilized Granules prepared from liquid composition composed of: | |
| 1 | Desloratadine | 16.45 |
| 2 | Resin | 33.0 |
| 3 | Malto dextrin | 110.0 |
| 4 | Citric acid | 5.0 |
| 5 | Water | q.s. to 658 g |
| | Blend Composition | |
| 6 | Citric acid | 3.0 |
| 7 | Magnesium stearate | 2.5 |

Comparative Example I

A comparative pharmaceutical formulation was prepared essentially as described in Example 2 by using a blend composition containing Talc, Magnesium stearate and the other following ingredients:

| | Ingredients | Quantity per 1000 Stick Packs (g) |
|---|---|---|
| | Lyophilized Granules prepared from liquid composition composed of: | |
| 1 | Desloratadine | 16.45 |
| 2 | Resin | 33.0 |
| 3 | Malto dextrin | 110.0 |
| 4 | Citric acid | 5.0 |
| 5 | Water | q.s. to 658 mg |
| | Blend Composition | |
| 6 | Citric acid | 3.0 |
| 7 | Talc | 1.3 |
| 8 | Magnesium stearate | 1.3 |

Comparative Example J

A comparative pharmaceutical formulation was prepared essentially as described in Example 2 by using a blend composition containing only liquid paraffin and the other following ingredients:

| | Ingredients | Quantity per 1000 Stick Packs (g) |
|---|---|---|
| | Lyophilized Granules prepared from liquid composition composed of: | |
| 1 | Desloratadine | 16.45 |
| 2 | Resin | 33.0 |
| 3 | Malto dextrin | 127.0 |
| 4 | Citric acid | 5.0 |
| 5 | Water | q.s. to 200 g |
| | Blend Composition | |
| 6 | Citric acid | 3.0 |
| 7 | Liquid paraffin | 2.5 |

Comparative Example K

A comparative pharmaceutical formulation was prepared essentially as described in Example 2 by using a blend composition containing only Sorbitol and the other following ingredients:

| Ingredients | Quantity per 1000 Stick Packs (g) |
|---|---|
| Lyophilized Granules prepared from liquid composition composed of: | |
| 1  Desloratadine | 10.0 |
| 2  Resin | 20.0 |
| 3  Malto dextrin | 67.0 |
| 4  Citric acid | 3.0 |
| 5  Water | q.s. to 400 g |
| Blend Composition | |
| 6  Sorbitol | 400.0 |

Example 3: Sildenafil Composition

A formulation of sildenafil was prepared using the following ingredients:

| Ingredients | Quantity per 1000 Stick Packs (g) |
|---|---|
| Lyophilized Granules prepared from liquid composition composed of: | |
| 1  Sildenafil Citrate | 140.48 |
| 2  Sodium hydroxide | 30.12 |
| 3  Mannitol | 149.45 |
| 4  HPC-L | 4.0 |
| 5  Purified Water | q.s to 1000 g |
| Blend Composition | |
| 6  Sorbitol | 604.87 |
| 7  Citric acid | 64.63 |
| 8  Liquid paraffin | 3.0 |

Manufacturing Procedure

I. Lyophilized Granules
1. Sodium hydroxide was dissolved in 370 mL of purified water under stirring on overhead stirrer for 10 min at 1000 RPM
2. Sildenafil citrate was dispersed uniformly in the solution of step 1 under stirring for 30 min.
3. The dispersion obtained in step 2 was homogenized at 10000 RPM for 60 min using homogenizer and overhead stirrer.
4. Hydroxypropyl cellulose L was dissolved in water (166.5 g) and the solution was added to dispersion of step 2 under stirring.
5. Mannitol was added to the dispersion.
6. The final weight of the solution/dispersion was made to 1000 g using purified water.
7. Mixing of the solution/dispersion was continued for 10 minutes in a magnetic/overhead stirrer.
8. This solution/dispersion was filled in stainless steel tray and freeze-dried in a lyophilizer.
9. After complete freeze drying, the lyophilized cake was sieved through a #40 sieve to obtain the lyophilized granules.

II. Blend Composition
10. Sorbitol was passed through a #40 sieve and mixed with crushed and sieved citric acid in a double cone blender for 2 minutes at 10 RPM.
11. Liquid paraffin was added dropwise to 40 g of the mixture from step 10, and mixed manually to obtain a uniformly distributed blend composition.
12. The blend composition was sieved through a #60 sieve and then mixed with remaining mixture from step 9 using a double cone blender for 3 minutes at 10 RPM to obtain the final blend composition.

III. Formulation
13. The lyophilized granules from step 9 were mixed with the final blend composition from step 12 in a double cone blender for 5 minutes at 10 RPM to obtain the free flowing Sildenafil Citrate formulation.
14. The free flowing formulation was filled into stick packs and sealed, at 500 or 1000 mg per stick pack (see FIG. 5).

Example 4: Sildenafil Composition

A formulation of Sildenafil was prepared essentially as described in Example 3 using the following ingredients:

| Ingredients | Quantity per 1000 Stick Packs (g) |
|---|---|
| Lyophilized Granules prepared from liquid composition composed of: | |
| 1  Sildenafil Citrate | 140.48 |
| 2  Sodium hydroxide | 30.12 |
| 3  Mannitol | 149.45 |
| 4  HPC-L | 4.0 |
| 5  Purified Water | q.s to 1000 g |
| Blend Composition | |
| 6  Sorbitol | 604.87 |
| 7  Tartaric acid pellets | 64.63 |
| 8  Liquid paraffin | 3.00 |

Comparative Example L

A granule formulation was prepared essentially as described in Example 3 using the following ingredients:

| Ingredients | Quantity per 1000 Stick Packs (g) |
|---|---|
| 1  Sildenafil Citrate | 140.48 |
| 2  Sodium hydroxide | 30.12 |
| 3  Mannitol | 149.45 |
| 4  HPC-L | 4.0 |
| 5  Purified Water | q.s to 1000 g |

Comparative Example M

A comparative pharmaceutical formulation was prepared essentially as described in Example 3 by using a blend composition containing talc and the other following ingredients:

| Ingredients | Quantity per 1000 Stick Packs (g) |
|---|---|
| Lyophilized Granules prepared from liquid composition composed of: | |
| 1  Sildenafil Citrate | 140.48 |
| 2  Sodium hydroxide | 30.12 |
| 3  Mannitol | 149.45 |
| 4  HPC-L | 4.0 |
| 5  Purified Water | q.s to 1000 g |
| Blend Composition | |
| 6  Citric acid | 64.63 |
| 7  Talc | 3.0 |

Comparative Example N

A comparative pharmaceutical formulation was prepared essentially as described in Example 3 by using a blend composition containing Magnesium stearate and the other following ingredients:

| Ingredients | Quantity per 1000 Stick Packs (g) |
|---|---|
| Lyophilized Granules prepared from liquid composition composed of: | |
| 1  Sildenafil Citrate | 140.48 |
| 2  Sodium hydroxide | 30.12 |
| 3  Mannitol | 149.45 |
| 4  HPC-L | 4.0 |
| 5  Purified Water | q.s to 1000 g |
| Blend Composition | |
| 6  Citric acid | 64.63 |
| 7  Magnesium stearate | 3.0 |

Comparative Example O

A comparative pharmaceutical formulation was prepared essentially as described in Example 3 by using a blend composition containing Talc, Magnesium stearate and the other following ingredients:

| Ingredients | Quantity per 1000 Stick Packs (g) |
|---|---|
| Lyophilized Granules prepared from liquid composition composed of: | |
| 1  Sildenafil Citrate | 140.48 |
| 2  Sodium hydroxide | 30.12 |
| 3  Mannitol | 149.45 |
| 4  HPC-L | 4.0 |
| 5  Purified Water | q.s to 1000 g |
| Blend Composition | |
| 6  Citric acid | 64.63 |
| 7  Talc | 1.50 |
| 8  Magnesium stearate | 1.50 |

Comparative Example P

A comparative pharmaceutical formulation was prepared essentially as described in Example 3 by using a blend composition containing liquid paraffin and the other following ingredients:

| Ingredients | Quantity per 1000 Stick Packs (g) |
|---|---|
| Lyophilized Granules prepared from liquid composition composed of: | |
| 1  Sildenafil Citrate | 140.48 |
| 2  Sodium hydroxide | 30.12 |
| 3  Mannitol | 149.45 |
| 4  HPC-L | 4.0 |
| 5  Purified Water | q.s to 1000 g |
| Blend Composition | |
| 6  Citric acid | 64.63 |
| 7  Liquid paraffin | 3.0 |

Comparative Example Q

A comparative pharmaceutical formulation was prepared essentially as described in Example 3 by using a blend composition containing Sorbitol and the other following ingredients:

| Ingredients | Quantity per 1000 Stick Packs (g) |
|---|---|
| Lyophilized Granules prepared from liquid composition composed of: | |
| 1  Sildenafil Citrate | 140.48 |
| 2  Sodium hydroxide | 30.12 |
| 3  Mannitol | 149.45 |
| 4  HPC-L | 4.0 |
| 5  Purified Water | q.s to 1000 g |
| Blend Composition | |
| 6  Sorbitol | 604.87 |

Example 5: Solifenacin Composition

A formulation of Solifenacin was prepared using the following ingredients:

| Ingredients | Quantity per 1000 Stick Packs (g) |
|---|---|
| Lyophilized Granules prepared from liquid composition composed of: | |
| 1  Solifenacin | 10.0 |
| 2  Polacrillin Potassium (Resin) | 20.0 |
| 3  Malto dextrin | 67.0 |
| 4  Citric acid | 3.0 |
| 5  Water | q.s. to 400 g |
| Blend Composition | |
| 6  Sorbitol | 394.5 |
| 7  Citric acid | 3.0 |
| 8  Liquid paraffin | 2.5 |

Manufacturing Procedure

I. Lyophilized Granules
 1. Solifenacin was dissolved in 140 g of water using a magnetic/overhead stirrer for 5 minutes.
 2. Citric acid was added under continuous stirring using a magnetic/overhead stirrer.
 3. Resin was added under continuous stirring and the dispersion formed was kept under stirring for 1 hour.
 4. Maltodextrin was dissolved in 140 g of water in separate beaker & then added in to step 3 under continuous stirring.
 5. The final weight of the solution/dispersion was made to 400 g using purified water.
 6. Mixing of the solution/dispersion was continued for 10 minutes in a magnetic/overhead stirrer.
 7. This solution/dispersion was filled in stainless steel tray and freeze-dried in a lyophilizer.
 8. After complete freeze drying, the lyophilized cake was sieved through a #40 sieve to obtain the lyophilized granules.

II. Blend Composition
 9. Sorbitol was passed through a #40 sieve and mixed with crushed and sieved citric acid in a double cone blender for 2 minutes at 10 RPM.
 10. Liquid paraffin was added dropwise to 40 g of the mixture from step 9, and mixed manually to obtain a uniformly distributed blend composition.
 11. The blend composition was sieved through a #60 sieve and then mixed with remaining mixture from step 9 using a double cone blender for 3 minutes at 10 RPM to obtain the final blend composition.

III. Formulation

12. The lyophilized granules from step 8 were mixed with the final blend composition from step 11 in a double cone blender for 5 minutes at 10 RPM to obtain the free flowing Solifenacin formulation.
13. The free flowing composition was filled into stick packs and sealed, at 500 mg per stick pack (see FIG. 5).

Comparative Example R

A granule formulation was prepared essentially as described in Example 5 using the following ingredients:

| | Ingredients | Quantity per 1000 Stick Packs (g) |
|---|---|---|
| 1 | Solifenacin | 16.5 |
| 2 | Polacrillin Potassium (Resin) | 33.0 |
| 3 | Malto dextrin | 110.5 |
| 4 | Citric acid | 5.0 |
| 5 | Water | q.s. to 682 g |

Comparative Example S

A comparative pharmaceutical formulation was prepared essentially as described in Example 5 by using a blend composition containing talc and the other following ingredients:

| | Ingredients | Quantity per 1000 Stick Packs (g) |
|---|---|---|
| Lyophilized Granules prepared from liquid composition composed of: | | |
| 1 | Solifenacin | 16.5 |
| 2 | Polacrillin Potassium (Resin) | 33.0 |
| 3 | Malto dextrin | 110.5 |
| 4 | Citric acid | 5.0 |
| 5 | Water | q.s. to 682 g |
| Blend Composition | | |
| 6 | Citric acid | 3.0 |
| 7 | Talc | 2.5 |

Comparative Example T

A comparative pharmaceutical formulation was prepared essentially as described in Example 5 by using a blend composition containing Magnesium stearate and the other following ingredients:

| | Ingredients | Quantity per 1000 Stick Packs (g) |
|---|---|---|
| Lyophilized Granules prepared from liquid composition composed of: | | |
| 1 | Solifenacin | 16.5 |
| 2 | Polacrillin Potassium (Resin) | 33.0 |
| 3 | Malto dextrin | 110.5 |
| 4 | Citric acid | 5.0 |
| 5 | Water | q.s. to 682 g |
| Blend Composition | | |
| 6 | Citric acid | 3.0 |
| 7 | Magnesium stearate | 2.5 |

Comparative Example U

A comparative pharmaceutical formulation was prepared essentially as described in Example 5 by using a blend composition containing Talc, Magnesium stearate and the other following ingredients:

| | Ingredients | Quantity per 1000 Stick Packs (g) |
|---|---|---|
| Lyophilized Granules prepared from liquid composition composed of: | | |
| 1 | Solifenacin | 16.5 |
| 2 | Polacrillin Potassium (Resin) | 33.0 |
| 3 | Malto dextrin | 110.5 |
| 4 | Citric acid | 5.0 |
| 5 | Water | q.s. to 682 g |
| Blend Composition | | |
| 6 | Citric acid | 3.0 |
| 7 | Talc | 1.3 |
| 8 | Magnesium stearate | 1.3 |

Comparative Example V

A comparative pharmaceutical formulation was prepared essentially as described in Example 5 by using a blend composition containing liquid paraffin and the other following ingredients:

| | Ingredients | Quantity per 1000 Stick Packs (g) |
|---|---|---|
| Lyophilized Granules prepared from liquid composition composed of: | | |
| 1 | Solifenacin | 16.5 |
| 2 | Polacrillin Potassium (Resin) | 33.0 |
| 3 | Malto dextrin | 110.5 |
| 4 | Citric acid | 5.0 |
| 5 | Water | q.s. to 682 g |
| Blend Composition | | |
| 6 | Citric acid | 3.0 |
| 7 | Liquid paraffin | 2.5 |

Comparative Example W

A comparative pharmaceutical formulation was prepared essentially as described in Example 5 by using a blend composition containing Sorbitol and the other following ingredients:

| | Ingredients | Quantity per 1000 Stick Packs (g) |
|---|---|---|
| Lyophilized Granules prepared from liquid composition composed of: | | |
| 1 | Solifenacin | 10.0 |
| 2 | Polacrillin Potassium (Resin) | 20.0 |
| 3 | Malto dextrin | 67.0 |
| 4 | Citric acid | 3.0 |
| 5 | Water | q.s. to 400 g |
| Blend Composition | | |
| 6 | Sorbitol | 400.0 |

Example 6: Bulk Density & Tapped Density Results

Bulk and tapped density are important to understand flow properties of formulations. The bulk density of a material is the ratio of the mass to the volume (including the interparticulate void volume) of an untapped powder sample. The tapped density is an increased bulk density attained after mechanically tapping a container containing the powder sample. The tapped density is obtained by mechanically tapping a graduated cylinder containing the sample until little further volume change is observed. Because the interparticulate interactions influencing the bulking properties of a powder are also the interactions that interfere with powder flow, a comparison of the bulk and tapped densities can give a measure of the relative importance of these interactions in a given powder. Such a comparison is often used as an index of the ability of the powder to flow, for example the Compressibility Index or the Hausner Ratio:

Compressibility Index (Carr Index):

$$\frac{100(V_0 - V_f)}{V_0}$$

Hausner Ratio:

$$\frac{V_0}{V_f}$$

$V_0$=unsettled apparent volume (bulk volume) $V_f$=final tapped volume

The lower the values of Compressibility Index and Hausner Ratio, the better the flow properties of the powder.

Procedure for Determining Bulk Density:

According to US Pharmacopoeia (USP) Chapter <616>, Method I, using a 100-mL cylinder readable to 1 mL and an amount of powder such that its untapped apparent volume is between 50 and 100 mL.

Procedure for determining Tapped Density:

According to US Pharmacopoeia (USP) Chapter <616>, Method I, with the following details:

A 100-mL graduated cylinder (readable to 1 mL) weighing 130±16 g is mounted on a holder weighing 240±12 g.

10, 500, and 1250 taps on the powder sample are conducted and corresponding volumes $V_{10}$, $V_{500}$, and $V_{1250}$ to the nearest graduated unit are measured.

If the difference between $V_{500}$ and $V_{1250}$ is less than or equal to 1 mL, $V_{1250}$ is the tapped volume.

If the difference between $V_{500}$ and $V_{1250}$ exceeds 1 mL, the measurement is repeated in increments such as 1250 taps, until the difference between succeeding measurements is less than or equal to 1 mL.

Results:

| Formulations | Bulk Density (g/ml) | Tapped Density (g/ml) | Carr Index | Hausner Ratio |
| --- | --- | --- | --- | --- |
| Example 1 | 0.476 | 0.652 | 26.984 | 1.370 |
| Example 2 | 0.50 | 0.64 | 21.67 | 1.28 |
| Comparative Example A | 0.192 | 0.333 | 42.308 | 1.733 |
| Comparative Example B | 0.200 | 0.341 | 41.333 | 1.705 |
| Comparative Example C | 0.231 | 0.385 | 40.000 | 1.667 |
| Comparative Example D | 0.208 | 0.366 | 43.056 | 1.756 |
| Comparative Example E | 0.160 | 0.273 | 41.489 | 1.709 |
| Comparative Example F | 0.24 | 0.37 | 33.87 | 1.51 |
| Comparative Example G | 0.24 | 0.41 | 41.27 | 1.70 |
| Comparative Example H | 0.27 | 0.39 | 30.91 | 1.45 |
| Comparative Example I | 0.26 | 0.39 | 34.48 | 1.53 |
| Comparative Example J | 0.21 | 0.41 | 49.32 | 1.97 |
| Comparative Example K | 0.44 | 0.63 | 29.41 | 1.42 |
| Example 3 | 0.417 | 0.690 | 39.69 | 1.655 |
| Example 4 | 0.444 | 0.714 | 37.77 | 1.607 |
| Comparative Example L | 0.278 | 0.488 | 43.065 | 1.756 |
| Comparative Example M | 0.308 | 0.541 | 43.07 | 1.757 |
| Comparative Example N | 0.323 | 0.556 | 41.93 | 1.722 |
| Comparative Example O | 0.323 | 0.541 | 40.32 | 1.676 |
| Comparative Example P | 0.286 | 0.513 | 44.28 | 1.795 |
| Comparative Example Q | 0.408 | 0.667 | 38.77 | 1.633 |
| Example 5 | 0.429 | 0.667 | 35.714 | 1.556 |
| Comparative Example R | 0.217 | 0.375 | 42.029 | 1.725 |
| Comparative Example S | 0.224 | 0.395 | 43.284 | 1.763 |
| Comparative Example T | 0.238 | 0.395 | 39.683 | 1.658 |
| Comparative Example U | 0.238 | 0.395 | 39.683 | 1.658 |
| Comparative Example V | 0.188 | 0.375 | 50.000 | 2.000 |
| Comparative Example W | 0.435 | 0.667 | 34.783 | 1.533 |

Example 7: Angle of Repose

The angle of repose has been used to characterize the flow properties of solids. Angle of repose is a characteristic related to interparticulate friction or resistance to movement between particles. The angle of repose is a constant, three-dimensional angle (relative to the horizontal base) assumed by a cone-like pile of material.

Procedure (as Per USP General Chapter <1174>):

The angle of repose is formed on a fixed base with a retaining lip to retain a layer of powder on the base. The base should be free of vibration. The height of the funnel is varied to carefully build up a symmetrical cone of powder. Care should be taken to prevent vibration as the funnel is moved. The funnel height should be maintained approximately 2-4 cm from the top of the powder pile as it is being formed in order to minimize the impact of falling powder on the tip of the cone. If a symmetrical cone of powder cannot be successfully or reproducibly prepared, this method is not appropriate. The angle of repose is determined by measuring the height of the cone of powder and calculating the angle of repose (a) from the following equation: tan (a)=height/0.5 base.

Results:

| Formulations | Angle of repose (degree) | Flow behavior |
| --- | --- | --- |
| Example 1 | 34 | Good |
| Example 2 | 36.66 | Fair |
| Comparative Example A | These formulations did not pass through the | |
| Comparative Example B | funnel as such due to rat hole formation and | |
| Comparative Example C | poor flow properties and hence could | |
| Comparative Example D | not be analyzed | |
| Comparative Example E | | |
| Comparative Example F | | |
| Comparative Example G | | |
| Comparative Example H | | |
| Comparative Example I | | |
| Comparative Example J | | |
| Comparative Example K | 41.10 | weak |
| Example 3 | 34 | Good |
| Example 4 | 35 | Good |

21
-continued

| Formulations | Angle of repose (degree) | Flow behavior |
|---|---|---|
| Comparative Example L | 37 | Fair |
| Comparative Example M | Formulations did not pass through the funnel as such due to rat hole formation and poor flow properties and hence could not be analyzed | |
| Comparative Example N | | |
| Comparative Example O | 36 | Fair |
| Comparative Example P | Formulations did not pass through the funnel as such due to rat hole formation and poor flow properties and hence could not be analyzed | |
| Comparative Example Q | 32 | Good |
| Example 5 | 31 | Good |
| Comparative Example R | 36 | Fair |
| Comparative Example S | Formulations did not pass through the funnel as such due to rat hole formation and poor flow properties and hence could not be analyzed | |
| Comparative Example T | 36 | Fair |
| Comparative Example U | 37 | Fair |
| Comparative Example V | Formulations did not pass through the funnel as such due to rat hole formation and poor flow properties and hence could not be analyzed | |
| Comparative Example W | 35 | Good |

Example 8: Moisture Content

The pharmaceutical formulations were placed in open petri dishes, which were then placed in a Climacel maintained at 25° C./75% RH for simulating exposure to high humidity. The moisture content of each formulation was analyzed after 1, 2 and 6 hours in the Climacel. Moisture content was evaluated by using USP General Chapter 921—Water Determination method.

Results:

| Formulations | Moisture Content (wt %) | | | |
|---|---|---|---|---|
| | Initial | 1 hour | 2 hours | 6 hours |
| Example 1 | 1.19 | 2.27 | 3.65 | 6.82 |
| Example 2 | 1.49 | 3.08 | 5.80 | 7.88 |
| Comparative Example A | 4.24 | 5.33 | 8.10 | 12.49 |
| Comparative Example B | 4.40 | 5.12 | 8.31 | 13.11 |
| Comparative Example C | 4.57 | 5.77 | 6.98 | 13.28 |
| Comparative Example D | 4.11 | 5.45 | 8.67 | 14.54 |
| Comparative Example E | 4.34 | 5.48 | 7.96 | 13.64 |
| Comparative Example F | 5.30 | 6.97 | 10.60 | 14.54 |
| Comparative Example G | 5.31 | 8.16 | 11.65 | 15.23 |
| Comparative Example H | 4.95 | 7.77 | 9.96 | 14.11 |
| Comparative Example I | 5.10 | 7.91 | 9.78 | 14.23 |
| Comparative Example J | 6.32 | 9.00 | 10.92 | 14.57 |
| Comparative Example K | 1.66 | 4.60 | 5.86 | 9.77 |
| Example 3 | 2.1 | 3.01 | 4.45 | 10.95 |
| Example 4 | 2.09 | 2.89 | 4.68 | 11.39 |
| Comparative Example L | 4.73 | 6.72 | 9.12 | 14.24 |
| Comparative Example M | 4.08 | 5.94 | 7.57 | 12.92 |
| Comparative Example N | 4.07 | 6.69 | 7.9 | 12.75 |
| Comparative Example O | 4.1 | 5.83 | 8.26 | 13.43 |
| Comparative Example P | 4.03 | 6.54 | 8.54 | 13.41 |
| Comparative Example Q | 2.05 | 3.2 | 4.86 | 12.06 |
| Example 5 | 1.17 | 2.98 | 3.8 | 5.65 |
| Comparative Example R | 4.65 | 10.19 | 14.64 | 13 |
| Comparative Example S | 4.46 | 13.56 | 10.87 | 13.26 |
| Comparative Example T | 4.14 | 10.24 | 10.11 | 13.42 |
| Comparative Example U | 4.62 | 14.82 | 8.59 | 10.14 |
| Comparative Example V | 4.95 | 12.68 | 8.58 | 12.42 |
| Comparative Example W | 1.94 | 2.49 | 3.11 | 8.37 |

Example 9: Anti-Sticking Properties

The anti-sticking properties of the formulation was measured by determining the residual content using the following procedure:

Procedure:

The pharmaceutical formulations were filled uniformly in 10 stick packs made from flexible laminates as depicted in FIG. 5. The fill weight of each stick pack was noted down for further reference. Filled stick packs were sealed using a sealing machine. The sealed stick packs were kept on vibratory shifter for 30 minutes for entrapping the formulations into the corners of the stick pack. Each stick pack was opened by cutting from one sealed side. The formulation from each stick pack was removed and weighed on a calibrated balance to measure the amount of formulation recovered from each stick pack. The residual content was calculated using the following formula:

(Fill weight of stick pack)−(Content recovered from stick pack)=Residual content Results

| Formulations | % Residual content | Standard Deviation |
|---|---|---|
| Example 1 | 2.04 | 0.39 |
| Example 2 | 1.35 | 0.35 |
| Comparative Example A | 6.49 | 1.14 |
| Comparative Example B | 4.98 | 0.99 |
| Comparative Example C | 7.39 | 0.73 |
| Comparative Example D | 5.11 | 1.03 |
| Comparative Example E | 4.10 | 0.99 |
| Comparative Example F | 4.76 | 0.80 |
| Comparative Example G | 4.75 | 0.91 |
| Comparative Example H | 4.02 | 0.56 |
| Comparative Example I | 4.04 | 0.34 |
| Comparative Example J | 3.02 | 2.20 |
| Comparative Example K | 1.94 | 0.50 |
| Example 3 | 0.63 | 0.11 |
| Example 4 | 0.6 | 0.11 |
| Comparative Example L | 2.28 | 0.86 |
| Comparative Example M | 2.78 | 0.57 |
| Comparative Example N | 2.08 | 0.43 |
| Comparative Example O | 2.25 | 0.34 |
| Comparative Example P | 1.42 | 0.65 |
| Comparative Example Q | 0.96 | 0.20 |
| Example 5 | 2.15 | 0.22 |
| Comparative Example R | 4.72 | 1.22 |
| Comparative Example S | 8.19 | 3.88 |
| Comparative Example T | 10.65 | 4.50 |
| Comparative Example U | 10.68 | 5.85 |
| Comparative Example V | * Wet Mass with very poor flow | |
| Comparative Example W | 4.73 | 3.09 |

The invention claimed is:

1. A free-flowing solid pharmaceutical formulation comprising (i) lyophilized granules comprising a pharmaceutically active ingredient selected from the group consisting of desloratadine, montelukast, solifenacin, silodosin, sildenafil, and pharmaceutically acceptable salts thereof, wherein the lyophilized granules do not comprise liquid paraffin, and (ii) a blend composition comprising sorbitol, liquid paraffin, and, optionally, citric acid, wherein:
the formulation comprises 0.01% to 30% by weight of the pharmaceutically active ingredient, and 0% to 30% by weight of other pharmaceutically acceptable excipients, wherein the wt/wt ratio of pharmaceutically active ingredient to solid blend composition is 0.01-30:70-99.99; and
the blend composition comprises 90% to 99.9% by weight of sorbitol, 0.1% to 5% by weight of liquid paraffin, and, optionally, citric acid, made by a process comprising:
(a) forming the lyophilized granules comprising the pharmaceutically active ingredient;
(b) forming the blend composition comprising sorbitol, liquid paraffin and, optionally, citric acid; and
(c) mixing the blend composition obtained in step (b) with the lyophilized granules obtained in step (a).

2. The formulation according to claim 1 wherein the blend composition comprises citric acid.

3. The formulation according to claim 1, comprising 0.1% to 28% by weight of the pharmaceutically active ingredient, and 5% to 30% by weight of one or more other pharmaceutically acceptable excipients.

4. The formulation according to claim 1 wherein the blend composition comprises 96% to 99.5% by weight of sorbitol, 0.5% to 4% by weight of liquid paraffin, and 0.5% to 2% by weight of citric acid.

5. The formulation according to claim 1 wherein the blend composition consists of 95% to 99.9% by weight of sorbitol, 0.1% to 5% by weight of liquid paraffin, and 0% to 4% by weight of citric acid.

6. The formulation according to claim 1, wherein the pharmaceutically active ingredient is desloratadine.

7. The formulation according to claim 1, wherein the pharmaceutically active ingredient is sildenafil.

8. The formulation according to claim 1, wherein the pharmaceutically active ingredient is solifenacin.

9. A package containing the formulation according to claim 1.

10. The package according to claim 9 selected from the group consisting of a sachet and a stick pack.

11. The formulation according to claim 3, wherein the blend composition comprises 96% to 99.5% by weight of sorbitol, 0.5% to 4% by weight of liquid paraffin, and 0.5% to 2% by weight of citric acid.

12. The formulation according to claim 3, wherein the blend composition consists of 95% to 99.9% by weight of sorbitol, 0.1% to 5% by weight of liquid paraffin, and 0% to 4% by weight of citric acid.

13. A free-flowing solid pharmaceutical formulation comprising (i) lyophilized granules comprising a pharmaceutically active ingredient selected from the group consisting of desloratadine, montelukast, solifenacin, silodosin, sildenafil, and pharmaceutically acceptable salts thereof, and (ii) a blend composition comprising sorbitol, liquid paraffin, and, optionally, citric acid, wherein:
the formulation comprises 0.01% to 30% by weight of the pharmaceutically active ingredient, and 0% to 30% by weight of other pharmaceutically acceptable excipients, wherein the wt/wt ratio of pharmaceutically active ingredient to solid blend composition is 0.01-30:70-99.99; and
the blend composition comprises 90% to 99.9% by weight of sorbitol, 0.1% to 5% by weight of liquid paraffin, and, optionally, citric acid,
made by a process comprising:
(a) forming the lyophilized granules comprising the pharmaceutically active ingredient;
(b) forming the blend composition comprising sorbitol, liquid paraffin and, optionally, citric acid; and
(c) mixing the blend composition obtained in step (b) with the lyophilized granules obtained in step (a).

14. The formulation according to claim 13, wherein the blend composition comprises citric acid.

15. The formulation according to claim 13, wherein the blend composition comprises 96% to 99.5% by weight of sorbitol, 0.5% to 4% by weight of liquid paraffin, and 0.5% to 2% by weight of citric acid.

16. The formulation according to claim 13, wherein the blend composition consists of 95% to 99.9% by weight of sorbitol, 0.1% to 5% by weight of liquid paraffin, and 0% to 4% by weight of citric acid.

17. The formulation according to claim 13, comprising 0.1% to 28% by weight of the pharmaceutically active ingredient, and 5% to 30% by weight of one or more other pharmaceutically acceptable excipients.

18. The formulation according to claim 17, wherein the blend composition comprises 96% to 99.5% by weight of sorbitol, 0.5% to 4% by weight of liquid paraffin, and 0.5% to 2% by weight of citric acid.

19. The formulation according to claim 17, wherein the blend composition consists of 95% to 99.9% by weight of sorbitol, 0.1% to 5% by weight of liquid paraffin, and 0% to 4% by weight of citric acid.

20. The formulation according to claim 13, wherein the pharmaceutically active ingredient is desloratadine.

21. The formulation according to claim 13, wherein the pharmaceutically active ingredient is sildenafil.

22. The formulation according to claim 13, wherein the pharmaceutically active ingredient is solifenacin.

23. The formulation according to claim 1, wherein the blend composition does not comprise citric acid.

24. The formulation according to claim 13, wherein the blend composition does not comprise citric acid.

* * * * *